United States Patent
Lerche et al.

(10) Patent No.: US 10,583,209 B2
(45) Date of Patent: Mar. 10, 2020

(54) HYPERPOLARIZED 1-13C-1,1-BIS(ACETOXY(METHYL))-2,2'-CYCLOPROPANE AS METABOLIC MARKER FOR MR

(71) Applicant: BRACCO IMAGING S.P.A., Milan (IT)

(72) Inventors: Mathilde H. Lerche, Frederiksberg C (DK); Pernille Rose Jensen, Vaerlose (DK); Magnus Karlsson, Malmo (SE); Roberta Napolitano, Albiano d'Ivrea (IT); Claudia Cabella, Pecco (IT); Luigi Miragoli, Dovera (IT); Sonia Colombo Serra, Vigliano Biellese (IT); Fabio Tedoldi, Marzano (IT)

(73) Assignee: BRACCO IMAGING S.P.A., Milan (IT)

(*) Notice: Subject to any disclaimer, the term of this patent is extended or adjusted under 35 U.S.C. 154(b) by 0 days.

(21) Appl. No.: 16/363,193

(22) Filed: Mar. 25, 2019

(65) Prior Publication Data
US 2019/0275180 A1    Sep. 12, 2019

Related U.S. Application Data

(62) Division of application No. 14/902,447, filed as application No. PCT/EP2014/063842 on Jun. 30, 2014, now abandoned.

(30) Foreign Application Priority Data

Jul. 1, 2013  (EP) ..................... 13174504

(51) Int. Cl.
| | |
|---|---|
| A61B 5/055 | (2006.01) |
| A61K 51/04 | (2006.01) |
| A61K 49/10 | (2006.01) |
| A61B 5/00 | (2006.01) |
| C07B 59/00 | (2006.01) |
| C07C 69/007 | (2006.01) |

(52) U.S. Cl.
CPC .......... *A61K 51/0402* (2013.01); *A61B 5/055* (2013.01); *A61B 5/4848* (2013.01); *A61K 49/10* (2013.01); *C07B 59/001* (2013.01); *C07C 69/007* (2013.01); *A61K 2123/00* (2013.01); *C07B 2200/05* (2013.01); *C07C 2601/02* (2017.05)

(58) Field of Classification Search
None
See application file for complete search history.

(56) References Cited

U.S. PATENT DOCUMENTS

| | | | |
|---|---|---|---|
| 6,278,893 B1* | 8/2001 | Ardenkjær-Larson | A61K 49/08 600/420 |
| 7,271,268 B1 | 9/2007 | Suen et al. | |
| 8,198,038 B2 | 6/2012 | Paik et al. | |
| 2008/0260649 A1 | 10/2008 | Thaning et al. | |
| 2010/0226859 A1* | 9/2010 | Brindle | A61B 5/055 424/9.3 |

FOREIGN PATENT DOCUMENTS

| | | |
|---|---|---|
| WO | 99/35508 A1 | 7/1999 |
| WO | 02/36005 A1 | 5/2002 |
| WO | 2006/011809 A1 | 2/2006 |
| WO | 2009/077575 A1 | 6/2009 |
| WO | 2011/124672 A1 | 10/2011 |
| WO | 2012/102773 A2 | 8/2012 |

OTHER PUBLICATIONS

Park et al. (Neuor-Oncology 2010, 12, 133-144).*
Day S.E. et al., "Detecting tumor response to treatment using hyperpolarized 13C magnetic resonance imaging and spectroscopy," Nat Med 2007; 13:1382-1387.
European Search Report for European application No. 13174504.4, dated Nov. 20, 2013.
Gallagher F.A. et al.,"13C MR spectroscopy measurements of glutaminase activity in human hepatocellular carcinoma cells using hyperpolarized 13C-labeled glutamine," Magn Reson Med 2008; 60:253-257.
Gallagher F.A. et al., "Magnetic resonance imaging of pH in vivo using hyperpolarized 13C-labelled bicarbonate," Nature 2008; 453:940-943 and Full Methods available at www.nature.com/nature.
Gallagher F.A. et al., "Production of hyperpolarized [1,4-13C2]malate from [1,4-13C2]fumarate is a marker of cell necrosis and treatment response in tumors," Proc Natl Acad Sci USA 2009; 106:19801-19806.
House, H.O. et al., "The synthesis of spiropentane-d8," J. Org. Chem. 1956; 21:1487-1491.
Hu S. et al., "In vivo carbon-13 dynamic MRS and MRSI of normal and fasted rat liver with hyperpolarized 13C-pyruvate," Mol Imaging Biol 2009; 11:399-407.

(Continued)

*Primary Examiner* — Michael G. Hartley
*Assistant Examiner* — Melissa J Perreira
(74) *Attorney, Agent, or Firm* — Vivicar Law, PLLC

(57) ABSTRACT

1-$^{13}$C-1,1-Bis(acetoxy(methyl))-2,2'-cyclopropane of formula (I):

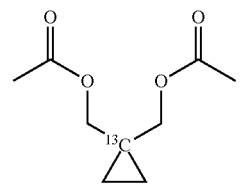

(I)

Figure 1:
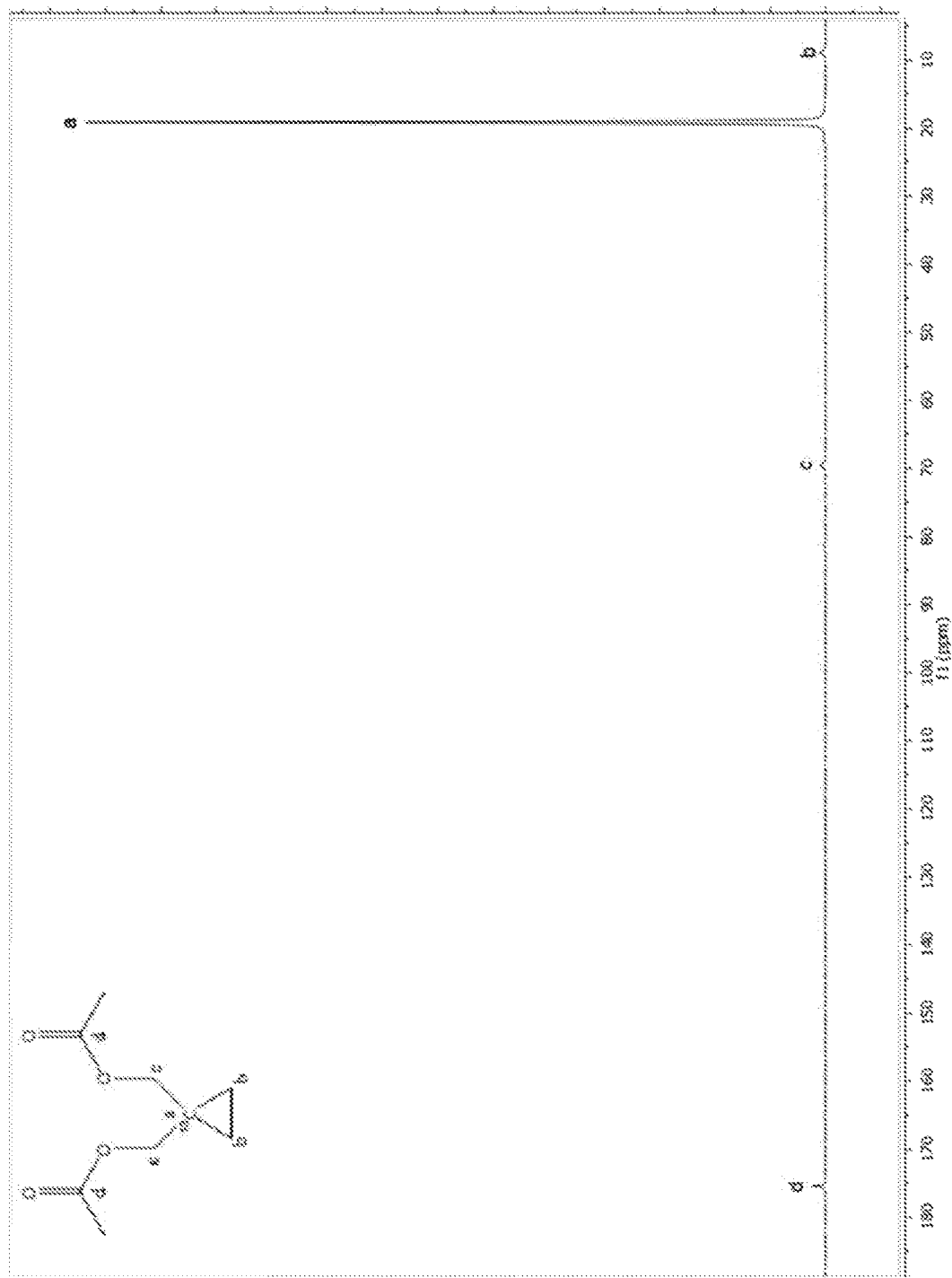

The compound can be hyperpolarized and used as a contrast agent in $^{13}$C Magnetic Resonance diagnostic technique ($^{13}$C-MR) for the diagnosis of tumor.

12 Claims, 5 Drawing Sheets

(56) References Cited

OTHER PUBLICATIONS

Imai T. "Human Carboxylesterase Isozymes: Catalytic Properties and Rational Drug Design," Drug Metab. Pharmacokinet 2006; 21(3): 173-85.

Jansen et al., "CPT-11 in human colon cancer cell lines and xenografts: characterization of cellular sensitivity determinants," Int. J. Cancer 1997; 70:335-40.

Jensen P.R. et al., "Tissue-specific short chain fatty acid metabolism and slow metabolic recovery after ischemia from hyperpolarized NMR in vivo," J Biol Chem 2009; 284:36077-36082.

Johansson, et al., "Cerebral perfusion assessment by bolus tracking using hyperpolarized 13C," Magn. Reson. Med. 51:464-472 (2004).

Karlsson M. et al., "Imaging of branched chain amino acid metabolism in tumors with hyperpolarized 13C ketoisocaproate," Int J Cancer 2010; 127:729-736.

Liewald et al, "Intracellular pH, esterase activity and DNA measurements of human lung carcinomas by flow cytometry," Cytometry 1990; 11: 341-48.

Merritt et al., "Hyperpolarized 13C allows a direct measure of flux through a single enzyme-catalyzed step by NMR," Proc Natl Acad Sci USA 2007; 104:19773-19777.

NA, K. et al., "Human plasma carboxylesterase 1, a novel serologic biomarker candidate for hepatocellular carcinoma," Proteomics 2009; 9: 3989-99.

PCT Search Report and Written Opinion for PCT/EP2014/063842, dated Sep. 29, 2014.

Rudakova et al., "Comparative analysis of esterase activities of human, mouse and rat blood," Bulletin of Experimental Biology and Medicine 2011; 152(1): 73-75.

Schroeder M.A. et al., "Measuring intracellular pH in the heart using hyperpolarized carbon dioxide and bicarbonate: a 13C and 31P magnetic resonance spectroscopy study," Cardiovasc Res 2010; 86:82-91.

Singh, R. K. et al., "Preparation of activated cyclopropanes by phase transfer alkylation," J. Org. Chem., 1975, 40 (20)2969-2970.

Talwar S., "The expression of human carboxylesterases in normal tissues and cancer cell lines," Master thesis, University of Southern California 2008; pp. 1-33.

Yan B. et al., "Rat serum carboxylesterase," Journal of Biological Chem. 1995; 270: 19128-34.

* cited by examiner

A

B

A

B

A

B

HYPERPOLARIZED 1-13C-1,1-BIS(ACETOXY(METHYL))-2,2'-CYCLOPROPANE AS METABOLIC MARKER FOR MR

CROSS-REFERENCE TO RELATED APPLICATIONS

This application is a divisional of U.S. application Ser. No. 14/902,447, filed Dec. 31, 2015, which is the national stage application of corresponding, international application number PCI/EP2014/063842, filed Jun. 30, 2014, which claims priority to and the benefit of European application no. 13174504.4 filed Jul. 1, 2013, all of which are hereby incorporated by reference in their entirety.

FIELD OF THE INVENTION

The invention relates to the field of Magnetic Resonance (MR), in particular to novel diagnostic media comprising hyperpolarized $1$-$^{13}$C-1,1-Bis(acetoxy(methyl))-2,2'-cyclopropane and to a diagnostic method exploiting said molecule as MR tracer.

BACKGROUND OF THE INVENTION

Magnetic resonance imaging (MRI) is a technique that has become particularly attractive to physicians as images of a patient's body or parts thereof can be obtained in a non-invasive way and without exposing the patient and the medical personnel to a potentially harmful radiation such as X-rays. Because of its high quality images and good spatial and temporal resolution. MRI is a favourable imaging technique for imaging soft tissue and organs. MRI may be carried out with or without MR contrast agents. However, contrast-enhanced MRI usually enables the detection of much smaller tissue changes, which makes it a powerful tool for the detection of early stage tissue changes like for instance small tumors or metastases.

MRI using hyperpolarized molecules is an emerging technique. WO 9935508 discloses a method of MR investigation of a patient using a hyperpolarized solution of a high $T_1$ agent as MRI contrast agent. The term "hyperpolarization" means enhancing the nuclear polarization of the NMR active nuclei present in the agent, i.e. nuclei with non-zero nuclear spin, preferably $^{13}$C- or $^{15}$N-nuclei, and thereby amplifying the MR signal intensity by a factor of hundred and more. When using a hyperpolarized $^{13}$C- and/or $^{15}$N-enriched high $T_1$ agent, there will be essentially no interference from background signals as the natural abundance of $^{13}$C and/or $^{15}$N is negligible and thus the image contrast will be advantageously high. The main difference between conventional MRI contrast agents and these hyperpolarized high $T_1$ agents is that in the former changes in contrast are caused by affecting the relaxation times of water protons in the body whereas the latter class of agents can be regarded as non-radioactive tracers, as the signal obtained arises solely from the agent. When hyperpolarization is obtained via a microwave assisted transfer between unpaired electrons and the nuclei used as MR probes, the techniques is referred as Dynamic Nuclear Polarization (DNP).

A variety of possible high $T_1$ agents for use as MR imaging agents are disclosed in WO9935508, including non-endogenous and endogenous compounds. As examples of the latter, intermediates in normal metabolic cycles are mentioned which are said to be preferred for imaging metabolic activity. By in vivo imaging of metabolic activity, information of the metabolic status of a tissue may be obtained and said information may for instance be used to discriminate between healthy and diseased tissue.

For example, WO 2009077575 discloses a method of $^{13}$C-MR detection using an imaging medium comprising hyperpolarized $^{13}$C-fumarate, in order to investigate both the citric acid and the urea cycles by detecting $^{13}$C-malate end optionally $^{13}$C-fumarate and/or $^{13}$C-succinate signals. The metabolic profile generated in a preferred embodiment of the method provides information about the metabolic activity of the body and part of the body under examination and said information may be used in a subsequent step for. e.g. identifying diseases. Such a disease is preferably cancer since tumor tissue is usually characterized by an altered metabolic activity. As a technical aspect, if the compounds to be polarized crystallize upon freezing or cooling their solution, a glass-forming additive must be added to the solution.

Dynamic nuclear polarization (DNP) has been applied recently to magnetic resonance spectroscopy (MRS) in solution, where it can be used to produce a large increase in sensitivity. Using this technique, the metabolism of several $^{13}$C-labeled compounds has been observed and used to estimate rate constants for specific enzyme-catalyzed reactions in vitro and in vivo (Day S E, Kettunen M I, Gallagher F A, Hu D E, Lerche M, Wolber J, Golman K, Ardenkjaer-Larsen J H, Brindle K M. Detecting tumor response to treatment using hyperpolerized $^{13}$C magnetic resonance imaging and spectroscopy. Nat Med 2007; 13:1382-1387; Gallagher F A, Kettunen M I, Hu D E, Jensen P R, Zandt R I, Karisson M, Gissetsson A, Nelson S K, Witney T H, Bohndiek S E, Hansson G, Peitersen T, Lerche M H, Brindle K M. Production of hyperpolarized [1.4-$^{13}$C$_2$]malate from [1,4-$^{13}$C$_2$]fumarate is a marker of cell necrosis and treatment response in tumors. Proc Nag Acad Sci USA 2009; 106: 19801-19806). Furthermore, for some hyperpolarized $^{13}$C-labeled substrates there is sufficient signal for the spatial distribution of both the substrate and its metabolites to be imaged in vivo. As some of these substrates have already been administered at relatively high concentrations in the clinic, this technique has the potential to be translated into clinical applications. To date, the most studied reactions have been those involving hyperpolarized [1-$^{13}$C]pyruvate: the hyperpolarized label can be exchanged with either endogenous lactate or alanine, or alternatively it can be irreversibly converted to carbon dioxide, which is subsequently converted to bicarbonate in the reaction catalyzed by carbonic anhydrase. These metabolic reactions have been observed in tumors, in cardiac tissue and in the liver (Merritt M E, Harrison C, Storey C, Jeffrey F M, Sherry A D, Malloy C R. Hyperpolarized $^{13}$C allows a direct measure of flux through a single enzyme-catalyzed step by NMR. Proc Natl Acad Sci USA 2007; 104:19773-19777; Schroeder M A, Swietach P, Atherton H J, Gallagher F A, Lee P, Radda G K, Clarke K, Tyler D J. Measuring intracellular pH in the heart using hyperpolarized carbon dioxide and bicarbonate: a $^{13}$C and $^{31}$P MRS study. Cardiovasc Res 2010; 86:82-91: Hu S, Chen A P, Zierhut M L, Bok R, Yen Y F, Schroeder M A, Hurd R E, Nelson S J, Kurhanewicz J, Vigneron D B. In vivo carbon-13 dynamic MRS and MRSI of normal and fasted rat liver with hyperpolarized $^{13}$C-pyruvate. Mol Imaging Bid 2009; 11:399-407).

Recently, other endogenous molecules have been successfully hyperpolarized: tumor pH has been measured in vivo from the relative concentrations of $^{13}$C-labeled bicarbonate and carbon dioxide following the injection of hyperpolarized $^{13}$C-labeled bicarbonate (Gallagher F A, Kettunen M I, Day S E, Hu D E, Ardenkjaer-Larsen J H, Zandt R, Jensen P R, Karlsson M, Golman K, Lerche M H, Brindle K M. Magnetic resonance imaging of pH in vivo using hyperpolarized $^{13}$C-labelled bicarbonate. Nature 2008; 453:940-943); elevated levels of hyperpolarized malate have been demonstrated in necrotic tumor tissue in vivo following the injection of hyperpolarized $^{13}$C-labeled fumarate (Gallagher F A, Kettunen M I, Hu D E, Jensen P R, Zandt R I, Karisson M, Gisselsson A, Nelson S K, Witney T H, Bohndiek S E, Hanason G, Peitersen T, Lerche M H, Brindle K M. Production of hyperpolarized [1,4-$^{13}$C$_2$]malate from [1,4-$^{13}$C$_2$] fumarate is a marker of cell necrosis and treatment response in tumors. Proc Natl Acad Sci USA 2009; 106:19801-19806); the metabolism of glutamine to glutamate, catalyzed by the mitochondrial enzyme glutaminase, has been observed following administration of hyperpolarized $^{13}$C-labeled glutamine to cells in vitro (Gallagher F A, Kettunen M I, Day S E, Lerche M, Brindle K M. $^{13}$C MR spectroscopy measurements of glutaminase activity in human hepatocellular carcinoma cells using hyperpolarized $^{13}$C-labeled glutamine. Magn Reson Med 2008; 60:253-257); the organ-specific metabolism of hyperpolarized $^{13}$C-labeled acetate to acetyl-CoA and acetyl carnitine has been observed in vivo (Jensen P R, Peitersen T, Karlsson M, In't Zandt R, Gisseisson A, Hansson G, Meier S, Lerche M H. Tissue-specific short chain fatty acid metabolism and slow metabolic recovery after ischemia from hyperpolarized NMR in vivo. J Biol Chem 2009:284:36077-36082), and the metabolism of branched chain amino acids has been observed in tumors following the addition of hyperpolarized $^{13}$C-labeled α-ketoisocaproate (Karisson M, Jensen P R, In't Zandt R, Gisselsson A, Hansson G, Duus J O, Meier S, Lerche M H. Imaging of branched chain amino acid metabolism in tumors with hyperpolarized $^{13}$C ketoisocaproate. Int J Cancer 2010: 127:729-736.10).

Although its etiology is lacking, cancer is phenomenologically well characterized as a molecular disease. Different kinds of cancers may have very different biochemical forms, however they can share general molecular features.

Early diagnosis of cancer continues to be given large attention since diagnosis at an early stage often increases the chances of a successful treatment. In fact, early diagnosing cancer and ensuring access to optimum treatment can lead to significant improvements in survival.

Early diagnosing of cancer could be achieved by taking advantage of a general molecular feature shared by different types of cancer cells and whose alteration in cancer can be early detected.

Carboxylesterases (CE, EC 3.1.1.1) are a family of enzymes catalysing the chemical conversion of an ester in an acid and an alcohol. A general reaction scheme is shown below:

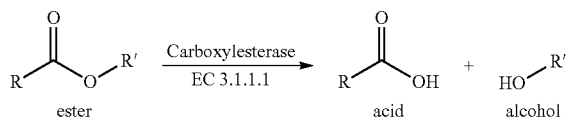

Carboxylesterases are ubiquitously expressed in mammalian tissues. The many CE isoforms have been classified into 5 super families (CE 1-5) based on amino acid homologies. The CE1 enzymes are mainly localized to the liver, however they are also expressed in most other tissue types. A rat specific CE1 isoform is secreted from the liver to the blood in rats and mice and this iso-enzyme is correlated to a high level of hydrolase activity detected in rodents compared to humans (Yan, B. Dongfang Y., Bullock, P., Parkinson, A., Rat serum carboxylesterases, 1995, *JBC,* 32 (270): 19128-34; Rudakova, E V., Botneva N P., Makhaeva, G F. Comparative analysis of esterase activities of human, mouse and rat blood, 2011, *Bulletin of experimental biology and medicine,* 152(1): 73-75). The other important isoform is the CE2 family, which is also expressed in the human liver (approx. 4 times less than CE1) as well as in most other tissues to a higher degree than CE1 (Talvar, S. The expression of human carboxylesterases in normal tissues and cancer cell lines (2008), Master thesis).

The expression of carboxylesterases decreases in cancer in both animal and human tissue. In particular, in hepatome cells a 4 times decrease in the expression of carboxyl esterase has been measured compared to normal hepatocytes. Dependent on the isoform the expression is reported to be approx. 1.5-4 times higher in normal tissue than in the corresponding malignant tissue (Talvar, 2008).

A number of studies have been reported on carboxylesterases in cancer cells.

The expression of carboxylesterase was reported as detectable in human cancer cells (HEPG2) and approx. 3-4 times lower than the expression of carboxyl esterase in normal human liver (hepatocytes) (Talvar, 2008). A patient study on non-tumor and tumor tissues from liver cancer (HCC) patients showed an almost 3 times decrease in the expression of carboxyl esterase in the tumor tissue (Na, K. et al., Human plasma carboxylesterase 1, a novel serologic biomarker candidate for hepatocellular carcinoma (2009). Proteomics, 9: 3989-99).

Another study showed that the carboxylesterase activity was significantly lower in colon cancer xenografts compared to the corresponding normal colon tissue in mice (Jansen et al., CPT-11 In human colon cancer cell lines and xenografts: characterization of cellular sensitivity determinants, 1997, Int. J. Cancer 70:335-40.)

A study has been reported on lung cancer patients where carboxylesterase activity is correlated to esterase expression in healthy and cancer lung tissue. In this study, they find that the activity correlates well with the expression, which is shown to be approx. 1.5 times higher in healthy tissue (Liewald F. et al, Intracellular pH, esterase activity and DNA measurements of human lung carcinomas by low cytometry, 1990, Cytometry, 11: 341-48)

WO2012102773 discloses a method for the diagnosis and treatment of cancer, in particular breast cancer, by measuring the activity of the enzyme PMPMEase (human carboxylesterase 1). Said activity is measured in a biological sample by assaying the enzyme expression or enzymatic activity, in the last case through the measurement of the consumption of a substrate or the production of a product. It is only generally stated that the enzyme assay can be performed in vivo.

U.S. Pat. No. 8,198,038 discloses a screening method to distinguish healthy human beings from those with human liver cancer (hepatocellular carcinoma: HCC) comprising the steps of collecting human blood and detecting the presence of human liver carboxylesterase 1 (hCE1) in the plasma, wherein the level of hCE1 protein is increased more in the plasma of patients with HCC than in the plasma of healthy patents.

The conversion of an hyperpolarized ester, catalysed by carboxylesterase, generates hyperpolarized metabolic products whose MR signals are well distinguishable from each other and from the injected substrate. Cancer cells and healthy cells convert a hyperpolarized ester to a different degree, leading to differences in said metabolic product signal amounts, therefore said difference between the signals in tumor and non-tumor cells can be exploited to identify cancer.

A common weakness of the endogenous molecules known in the prior art, when used as hyperpolarized markers, is the relatively fast vanishing of MR signals, of both the substrate itself and its relevant metabolites. DNP in fact, as well as all other hyperpolarization procedures, leads to a transient enhancement of the nuclear magnetic order, that allows the in vivo visualization of said moieties but, unfortunately, for a limited amount of time, in the order of 3 to 5 times the longitudinal relaxation time of the nuclei used as MR probe. Since MR imaging procedures require a certain amount of time in order for the final image to be reconstructed with acceptable sensitivity and resolution, markers with slower nuclear relaxation, with respect to the product used so far, are strongly desirable, also in view of inherent technical features of the imaging procedure, such as dilution (upon injection into patient) and metabolic conversion (time delay for achieving detectable concentrations of metabolites).

Therefore, in order to be able to register in vivo metabolic maps of tumour and healthy tissues, with superior sensitivity and resolution with respect to the state of the art, novel metabolic contrast agents with enhanced persistence of the hyperpolarized signal (i.e. slower nuclear longitudinal relaxation) are strongly needed.

SUMMARY OF THE INVENTION

It has now been found that $1\text{-}^{13}\text{C}\text{-}1,1\text{-Bis(acetoxy(methyl))-}2,2'$-cyclopropane is characterized by a $^{13}\text{C}$ longitudinal relaxation time significantly longer than any other known molecule used for metabolic imaging.

Said $1\text{-}^{13}\text{C}\text{-}1,1\text{-Bis(acetoxy(methyl))-}2,2'$-cyclopropane can be polarized by DNP in order to achieve a $^{13}\text{C}$ signal that allows its detection in vivo over an extended acquisition window. The conversion of said hyperpolarized ester, catalysed by carboxylesterase, generates hyperpolarized metabolic products whose MR signals are well distinguishable from each other and from the injected substrate.

Cancer cells and healthy cells convert $1\text{-}^{13}\text{C}\text{-}1,1\text{-Bis(acetoxy(methyl))-}2,2'$-cyclopropane to a different degree leading to differences in said metabolic product signal amounts, therefore said difference between the signals in tumor and non-tumor cells can be exploited to identify cancer.

Within the context of cancer diagnosis, said difference in the signals of hyperpolarized $1\text{-}^{13}\text{C}\text{-}1,1\text{-Bis(acetoxy(methyl))-}2,2'$-cyclopropane metabolized by a carboxylesterase can be used for detecting the presence of a tumor, for evaluating the efficacy of an anti-cancer therapy and/or to determine a time evolution of a tumor.

It has also been found that the overall hyperpolarized signal of the metabolites deriving from $1\text{-}^{13}\text{C}\text{-}1,1\text{-Bis(acetoxy(methyl))-}2,2'$-cyclopropane is far more intense than the hyperpolarized signal of the metabolites generating from $[1\text{-}^{13}\text{C}]$-pyruvate, the most used MR metabolic agent, in particular in some cancer cell types.

Therefore, an object of the present invention is the compound $1\text{-}^{13}\text{C}\text{-}1,1\text{-Bis(acetoxy(methyl))-}2,2'$-cyclopropane of formula (I):

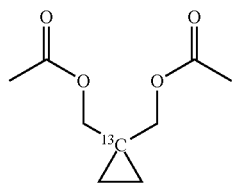

said compound being enriched above natural abundance of $^{13}\text{C}$ in position 1 of the molecule.

In a preferred embodiment, one or more hydrogen atoms of said $1\text{-}^{13}\text{C}\text{-}1,1\text{-Bis(acetoxy(methyl))-}2,2'$-cyclopropane are replaced by deuterium. More preferably, all the methylene groups of the compound of formula (I) are deuterated, the compound being thus identified as $1\text{-}^{13}\text{C}\text{-}1,1\text{-Bis(acetoxy(methyl-}d_2\text{))-}2,2'\text{-}d_4$-cyclopropane and having the following structural formula (II):

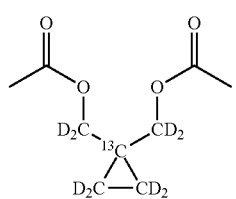

A process for the preparation of the new compound $1\text{-}^{13}\text{C}\text{-}1,1\text{-Bis(acetoxy(methyl))-}2,2'$-cyclopropane comprising the steps of:
 a) reacting $1\text{-}^{13}\text{C}\text{-}1,1\text{-Bis(hydroxy(methyl))-}2,2'$-cyclopropane with acetyl chloride, and
 b) removing the excess of acetyl chloride and the formed hydrochloric gas,
is also an object of the present invention.

The same process as above can be used for the preparation of deuterated $1\text{-}^{13}\text{C}\text{-}1,1\text{-Bis(acetoxy(methyl))-}2,2'$-cyclopropane by using in step a) deuterated $1\text{-}^{13}\text{C}\text{-}1,1\text{-Bis(hydroxy(methyl))-}2,2'$-cyclopropane.

The new compound can be hyperpolarized and used as a contrast agent in $^{13}\text{C}$ Magnetic Resonance diagnostic technique ($^{13}\text{C}$-MR) for the diagnosis of tumor.

It is also an object of the present invention a method of $^{13}\text{C}$-MR detection of tumors using an imaging medium comprising hyperpolarized $1\text{-}^{13}\text{C}\text{-}1,1\text{-Bis(acetoxy(methyl))-}2,2'$-cyclopropane, wherein signals of the corresponding hyperpolarized metabolic products of the carboxylesterase conversion are detected.

Said imaging medium comprising the hyperpolarized compound of the invention is also an object of the invention.

In a preferred embodiment of the present invention, the hyperpolarized metabolic products of carboxylesterase conversion of the compound of the invention are $1\text{-}^{13}\text{C}\text{-}1\text{-(acetoxy(methyl))-}1\text{-(hydroxy(methyl))-}2,2'$-cyclopropane and/or $1\text{-}^{13}\text{C}\text{-}1,1\text{-(dihydroxy(methyl))-}2,2'$-cyclopropane or a mixture thereof.

In a preferred embodiment, wherein the $1\text{-}^{13}\text{C}\text{-}1,1\text{-Bis(acetoxy(methyl))-}2,2'$-cyclopropane is deuterated, its metabolic products are also deuterated and they are indicated in the following description as $1\text{-}^{13}\text{C}\text{-}1\text{-(acetoxy(methyl-}d_2\text{))-}1\text{-(hydroxy(methy-}d_2\text{))-}2,2'\text{-}d_4$-cyclopropane and $1\text{-}^{13}\text{C}\text{-}1,1\text{-(dihydroxy(methyl-}d_2\text{))-}2,2'\text{-}d_4$-cyclopropane.

With respect to known hyperpolarized molecules used as metabolic markers, $1$-$^{13}$C-1,1-Bis(acetoxy(methyl))-2,2'-cyclopropane and its metabolic products $1$-$^{13}$C-1-(acetoxy(methyl))-1-(hydroxy(methyl))-2,2'-cyclopropane and $1$-$^{13}$C-1,1-(dihydroxy(methyl))-2,2'-cyclopropane have a much slower $^{13}$C MR signal decay, because of the unique quaternary position of the observed $^{13}$C nuclei which minimizes any longitudinal relaxation effect due to dipolar interaction and chemical shift anisotropy. This is a great advantage for metabolic imaging based on hyperpolarized markers, that reflects into more pronounced metabolite signals as well as on a broader time window for signal detection.

In an embodiment of the present invention, in the method of $^{13}$C-MR detection a first signal obtained from a region of interest is compared with a second signal (typically a signal derived from a reference sample, e.g. a signal obtained from a corresponding non-tumor/healthy tissue): said comparison is useful to determine a difference between tumor and non-tumor tissue. Said comparison can be used, for example, for the diagnosis of a tumor or to provide a localization of a tumor.

Furthermore, when a first signal obtained from a region of interest comprising a tumor tissue is compared with a second signal obtained from the same region of interest at an earlier time, the comparison between said first and said second signal can provide information about the tumor development over time, which can also be an indication of aggressiveness, of the tumor and/or the efficacy of a therapy when treating said tumor by (immune)pharmacological and/or surgical and/or radio therapy.

In a preferred embodiment of the invention, said first signal is the ratio between the signal of the metabolic product of the carboxylesterase conversion and the signal of the administered substrate (the hyperpolarized $1$-$^{13}$C-1,1-Bis(acetoxy(methyl))-2,2'-cyclopropane) detected in the region of interest and said second signal is the same ratio but detected in a reference sample, for example a corresponding non-tumor/healthy tissue, or in the same region at an earlier time.

Another object of the present invention is the above method of $^{13}$C-MR detection wherein said signals are used to generate a metabolic profile, based on the metabolic carboxylesterase conversion of hyperpolarized $1$-$^{13}$C-1,1-Bis(acetoxy(methyl))-2,2'-cyclopropane into the corresponding hyperpolarized metabolic products, wherein said metabolic profile is useful in detecting or providing indication of a tumor.

In an embodiment of the present invention, said metabolic profile is determined in a region of interest (where the presence of a tumor tissue is known or suspected) and compared with a metabolic profile of reference (e.g. relative to a corresponding non-tumor tissue, typically a healthy tissue in the close proximity of the tumor tissue).

Another object of the present invention is a method for operating an MRI system comprising the steps of:

a. submitting a subject who is affected or suspected to be affected by a tumor, who has been positioned in an MRI system and treated with hyperpolarized $1$-$^{13}$C-1,1-Bis(acetoxy(methyl))-2,2'-cyclopropane, and wherein said hyperpolarized $^{13}$C ester has been metabolically converted into the corresponding hyperpolarized metabolic product(s) of the carboxylesterase conversion, to a radio frequency pulse having a frequency selected to excite nuclear spin transitions in $^{13}$C nuclei;

b. recording an MR signal from said excited nuclei; and c. comparing a first MR signal deriving from a region of interest comprising said tumor or said suspected tumor with a second MR signal deriving from said subject or from a sample taken from said subject.

In an embodiment of the invention, said second signal is an MR-signal deriving from a non-tumor tissue of said subject. In another embodiment of the invention, said second signal is an MR-signal which has been detected from the region of interest, at an earlier time with respect to the first signal.

Another object of the invention is the above method further comprising the steps of:

d. determining a difference between said first signal and second signal;

e. comparing said difference of step d) with a reference value, to produce a deviation value; and f. determining if the deviation value is, in absolute value, higher than a predetermined value.

Another object of the present invention is the above method, wherein said second signal is determined on a non-tumor tissue, further comprising the step of:

g. providing an indication of possible tumor affection in case the deviation value is in absolute value higher than said predetermined value.

Another object of the present invention is the above method for operating an MRI system comprising steps a) to f), wherein said second signal is determined in the region of interest, at an earlier moment in time with respect to the first signal, and optionally stored in the system, said method further comprising the step of:

g'. providing an indication of tumor variation in case the deviation is in absolute value higher than said predetermined value.

Another object of the present invention is the above method for operating an MRI system comprising steps a) to f), wherein said subject has undergone an anti-tumor treatment and wherein said second signal is determined in the region of interest, at an earlier moment in time with respect to said first signal, and optionally stored in the system, said method further comprising the step of:

g". providing an indication of efficacy of said treatment if this deviation is in absolute value higher than a predetermined value.

In a preferred embodiment, said second signal is determined before, after or at the beginning of the treatment, wherein the effective time of detection of said second signal will be decided by the person skilled in the art, according to patient's conditions, kind of treatment, degree of severity of the disease and any other clinical parameter within the general knowledge on the matter. Examples of the time of determination of said second signal are few days, e.g. 1 to 5, one or more weeks, one or more months.

An MR system performing any of the methods above described is also an object of the present invention.

The use of said MR system for providing an indication of the presence of a tumor, of its grade of aggressiveness or for monitoring the response to an antitumor therapy of a subject affected by a tumor is also within the scope of the present invention.

The present invention provides the advantages of making available an imaging medium comprising hyperpolarized $1$-$^{13}$C-1,1-Bis(acetoxy(methyl))-2,2'-cyclopropane, which can be used in MRI technique for the diagnosis of tumors with a selective grade of distinction between tumor and non-tumor tissue.

A further advantage is represented by the possibility of taking different registrations of the MR signals of the hyperpolarized 1-$^{13}$C-1,1-Bis(acetoxy(methyl))-2,2'-cyclopropane in a tumor tissue, while an antitumor therapy is administered and to monitor the progress of the therapy.

A further advantage is represented by the possibility of detecting aggressive forms of tumors by monitoring the development of the formation of the corresponding $^{13}$C hyperpolarized metabolic product(s) of the carboxylesterase conversion in a tumor tissue.

These and other objects of the present invention and advantages will be disclosed in detail in the following description even by means of Figures and Examples.

FIGURES

FIG. 1. Dissolution spectrum of hyperpolarized 1-$^{13}$C-1,1-Bis(acetoxy(methyl-d$_2$))-2,2'-d$_4$-cyclopropane.

Figure 2:
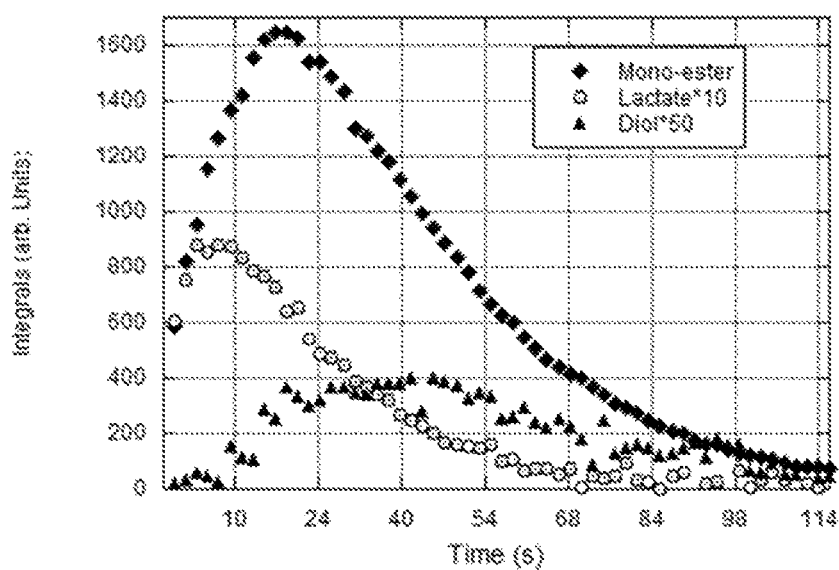
Figure 2:
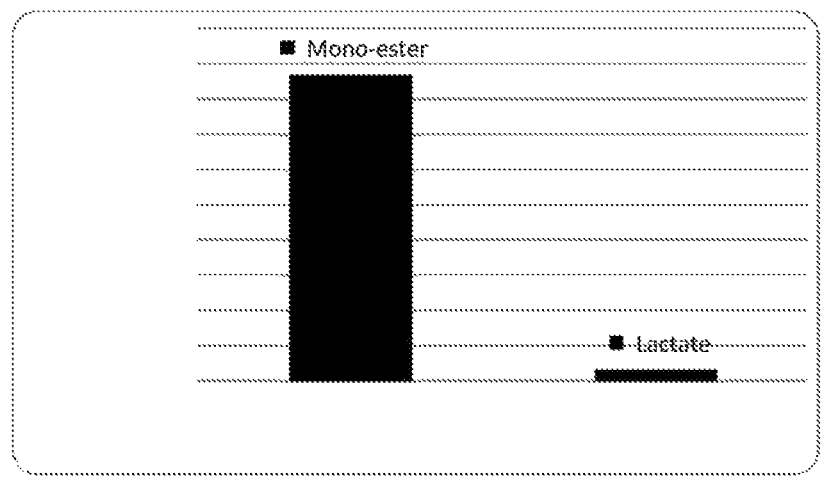

FIG. 2. In cell DNP conversion of 1-$^{13}$C-1,1-Bis(acetoxy(methyl-d$_2$))-2,2'-d$_4$-cyclopropane and 1-$^{13}$C pyruvate in rat liver cancer cells (rat hepatoma, Morris). The DNP experiments were performed with 10 million cells. A) Build-up of the metabolites 1-$^{13}$C-1-(acetoxy(methyl-d$_2$))-1-(hydroxy(methyl-d$_2$))-2,2'-d$_4$-cyclopropane and 1-$^{13}$C-1,1-(dihydroxy(methyl-d$_2$))-2,2'-d$_4$-cyclopropane from injection of 1-$^{13}$C-1,1-Bis(acetoxy(methyl-d$_2$))-2,2'-d$_4$-cyclopropane and of 1-$^{13}$C-lactate from injection of 1-$^{13}$C-pyruvate, respectively into whole Morris cells. B) Area under the curve of the metabolites 1-$^{13}$C-1-(acetoxy(methyl-d$_2$))-1-(hydroxy(methyl-d$_2$))-2,2'-d$_4$-cyclopropane and 1-$^{13}$C-lactate.

Figure 3:
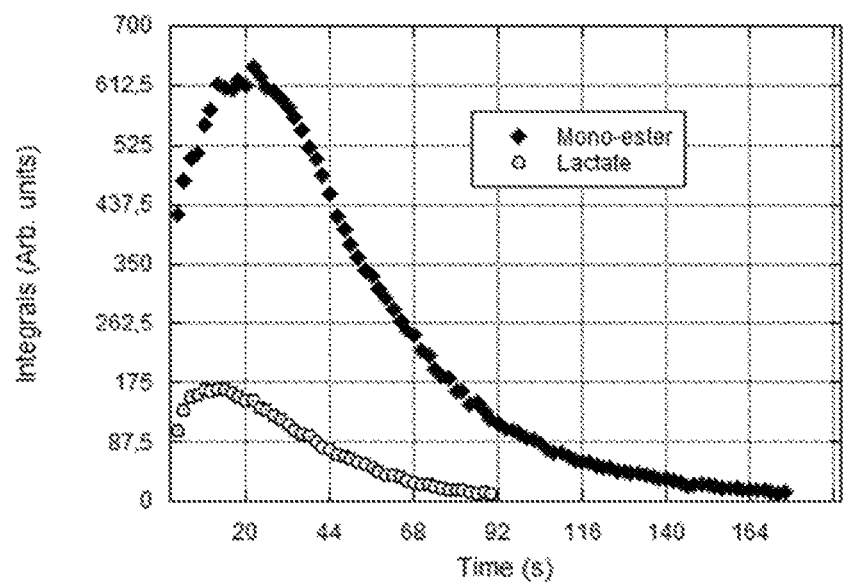
Figure 3:
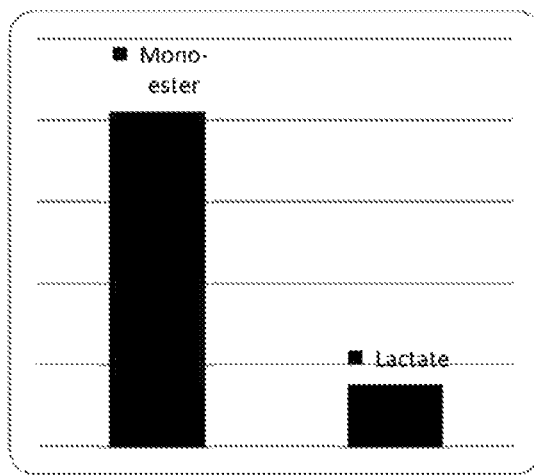

FIG. 3. In cell DNP conversion of 1-$^{13}$C-1,1-Bis(acetoxy(methyl-d$_2$))-2,2'-d$_4$-cyclopropane and 1-$^{13}$C pyruvate in human prostate cancer cells (human prostate carcinoma, PC-3). The DNP experiments were performed with 10 million cells. A) Build-up of the metabolites 1-$^{13}$C-1-(acetoxy(methyl-d$_2$))-1-(hydroxy(methyl-d$_2$))-2,2'-d$_4$-cyclopropane from injection of 1-$^{13}$C-1,1-Bis(acetoxy(methyl-d$_2$))-2,2'-d$_4$-cyclopropane and 1-$^{13}$C-lactate from injection of 1-$^{13}$C-pyruvate, respectively into whole PC-3 cells. B) Area under the curve of the metabolites 1-$^{13}$C-1-(acetoxy(methyl-d$_2$))-1-(hydroxy(methyl-d$_2$))-2,2'-d$_4$-cyclopropane and 1-$^{13}$C-lactate.

Figure 4:
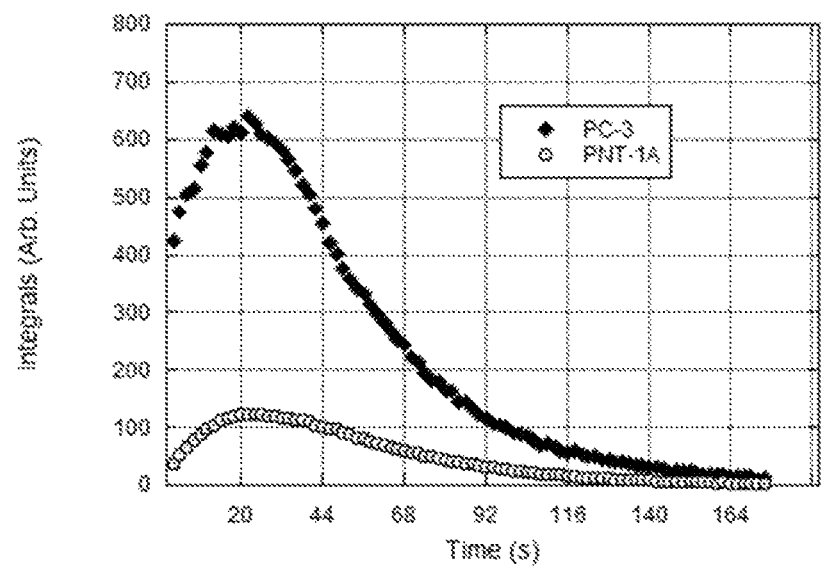
Figure 4:
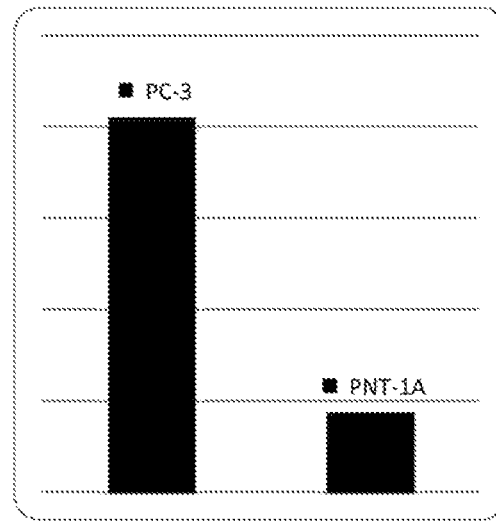

FIG. 4. In cell DNP conversion of 1-$^{13}$C-1,1-Bis(acetoxy(methyl-d$_2$))-2,2'-d$_4$-cyclopropane in human prostate cancer cells (human prostate carcinoma. PC-3) and in human prostate healthy cells (Immortalized human prostate cells, PNT-1A)). The DNP experiments were performed with 10 million cells. A) Build-up of the metabolite 1-$^{13}$C-1-(acetoxy(methyl-d$_2$))-1-(hydroxy(methyl-d$_2$))-2,2'-d$_4$-cyclopropane in PC-3 cells (filled squares) and in PNT-1A cells (open circles). B) Area under the curve of the metabolite 1-$^{13}$C-1-(acetoxy(methyl-d$_2$))-1-(hydroxy(methyl-d$_2$))-2,2'-d$_4$-cyclopropane produced in PC-3 cells and in PNT-1A cells.

Figure 5:
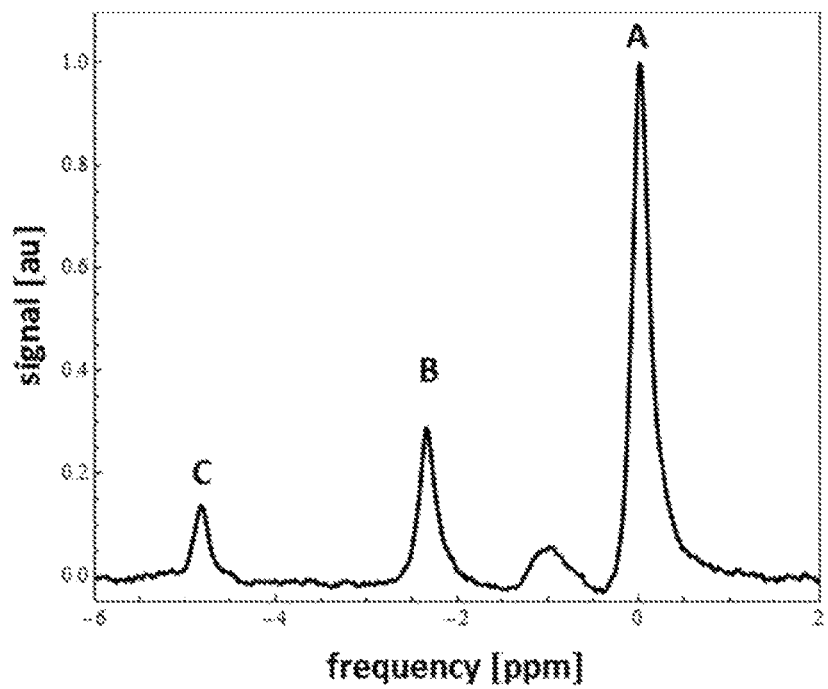

FIG. 5. $^{13}$C NMR sum spectrum, obtained by integrating over time the spectra of a time series acquired on the prostate of a representative animal, 1-$^{13}$C-1,1-Bis(acetoxy(methyl-d$_2$))-2,2'-d$_4$-cyclopropane is labelled as A, whereas the metabolites signals are labelled as B (1-$^{13}$C-1-(acetoxy(methyl-d$_2$))-1-(hydroxy(methyl-d$_2$))-2,2'-d$_4$-cyclopropane) and C (1-$^{13}$C-1,1-Bis(hydroxy(methyl))-2,2'-d$_4$-cyclopropane).

Figure 6:
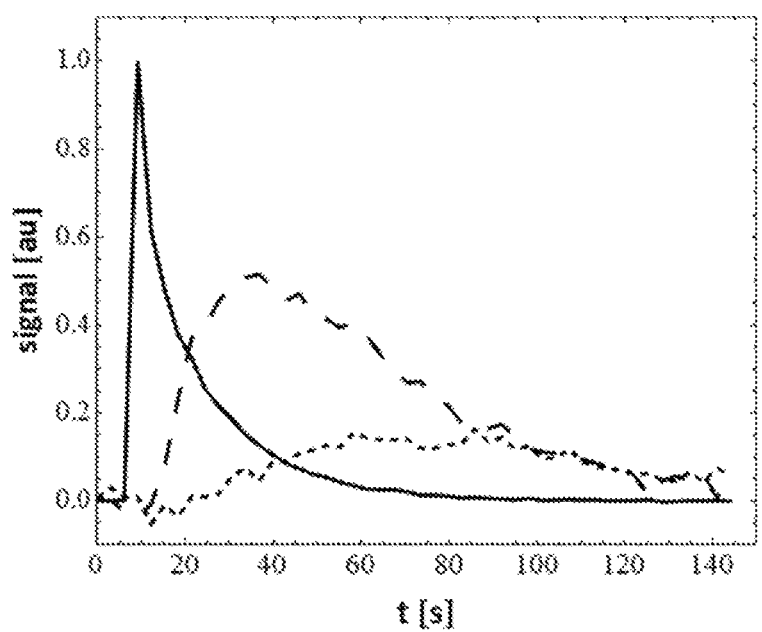

FIG. 6. Time course of the $^{13}$C NMR signals in rat prostates (average over n=2 subjects) after injection of 1-$^{13}$C-1,1-Bis(acetoxy(methyl-d$_2$))-2,2'-d$_4$-cyclopropane (solid line). The evolution of the metabolites signals is represented by a wide dashed line (1-$^{13}$C-1-(acetoxy(methyl-d$_2$))-1-(hydroxy(methy-d$_2$))-2,2'-d$_4$-cyclopropane) and by a narrow dashed line (1-$^{13}$C-1,1-Bis(hydroxy(methyl-d$_2$))-2,2'-d$_4$-cyclopropane) respectively.

DETAILED DESCRIPTION OF THE INVENTION

Within the scopes of the present invention, the term MRI means Imaging (typically for diagnostic purposes) by means of Magnetic Resonance (MR) as commonly intended in the state of the art and for example disclosed in WO200977575 and the references cited therein.

Within the scopes of the present invention, the "imaging medium" and "contrast agent" are used synonymously, as commonly intended in the state of the art and for example disclosed in WO200977575 and the references cited therein.

Within the scopes of the present invention, the terms "hyperpolarization", "hyperpolarized" or similar mean enhancing the nuclear polarization of NMR active nuclei present in the high T, agent as commonly intended in the state of the art and for example disclosed in WO200977575 and the references cited therein.

Within the scopes of the present invention, the term Dynamic Nuclear Polarization (DNP) is a technique in Magnetic Resonance Imaging as commonly intended in the state of the art and for example disclosed in WO200977575 and the references cited therein.

Within the meaning of the present invention, the term "hyperpolarized" means the nuclear spin polarization of a compound higher than thermal equilibrium.

Within the scope of the present invention "MRI system" means apparatus, equipment and all features and accessories useful for performing MR experiments, in particular for diagnostic purposes.

Within the meaning of the present invention, "1-$^{13}$C" means that the labeled compound is enriched in $^{13}$C in position 1 of the molecule. The term "enriched" means that the concentration of the non-zero nuclear spin nuclei in the compound (in particular of $^{13}$C in position 1) is above the typical value of natural abundance of said nuclei, preferably above at least 10% of natural abundance, more preferably above at least 25%, and even more preferably above at least 75% of its natural abundance and most preferably above at least 90% of its natural abundance. Enrichment can be achieved by chemical synthesis or biological labeling, according to the prior art teachings. Enrichment of non-zero nuclear spin nuclei over natural abundance may be determined, for instance, on a reference amount of the material, e.g. at least 0.1 mmole, preferably at least 1 mmole of the material.

The new compound 1-$^{13}$C-1,1-Bis(acetoxy(methyl))-2,2'-cyclopropane is synthesized starting from 1-$^{13}$C-1,1-Bis(hydroxy(methyl))-2,2'-cyclopropane according to methods known in the art, typically by esterifying the alcohol groups of the starting compound and isolating the final compound by any conventional means known in the art. For instance, acetyl chloride is added, preferably in excess, to the starting compound and the resulting mixture is stirred to obtain the desired product 1-$^{13}$C-1,1-Bis(acetoxy(methyl))-2,2'-cyclopropane. Preferably, the excess of acetyl chloride and the formed hydrochloric gas are removed from the mixture, and the final compound is isolated and recovered from the mixture.

The starting compound 1-$^{13}$C-1,1-Bis(hydroxy(methyl))-2,2'-cyclopropane can be obtained according to any preparation methods known in the art, starting from commercially available $^{13}$C-labelled diethyl malonate.

For instance, $^{13}$C-labelled diethyl malonate can be subjected to a double alkylation by reacting it with 1,2-dibromethane and subsequent reduction of the ester groups with LiAlH$_4$, according to the following reaction scheme:

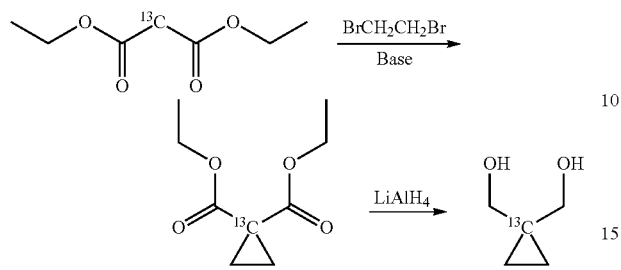

as described by House, H. O. et al. The synthesis of spiropentane-d8". J. Org. Chem. 1956, 21, 1487-149. Alternatively, diethyl malonate can be reacted with dihaloethane to provide a malonic acid derivative with a cyclopropyl group in 2-position, as described for instance by Singh R. K. and Danishefsky S., J. Org. Chem. 1975, 40(20), 2969-2970. The malonic acid derivative is then reduced as above described with LiAlH$_4$ to give the desired diol compound.

In a preferred embodiment of the process, the starting compound is deuterated 1-13C-1,1-Bis(hydroxy(methyl-d2))-2,2'-d4-cyclopropane which can be obtained as described above by reacting from a corresponding commercially available 13C-labelled diethyl malonate with respective deuterated reactants, i.e. BrCD2CD2Br and LiAlD4, both commercially available; according to the preparation methods described above (where the hydrogen atoms of the respective reactants are replaced by deuterium); the obtained product of the invention, 1-13C-1,1-Bis(acetoxy(methyl-d2))-2,2'-d4-cyclopropane, is thus also deuterated.

The 1-$^{13}$C-1,1-Bis(acetoxy(methyl))-2,2'-cyclopropane is hyperpolarized by Dynamic Nuclear Polarization (DNP), which is a known method disclosed, for example, in WO9935508, and in particular in WO2011124672. Hyperpolarized 1-$^{13}$C-1,1-Bis(acetoxy(methyl))-2,2'-cyclopropane is obtained. It can be used in an imaging medium. In a method of $^{13}$C-MR detection.

The activity of the carboxylesterase isoforms CE1 and CE2 is highly substrate dependent. In general substrates with a smaller alcohol group than acid group are reported to have higher affinity for the carboxylesterase isoform CE1 and the reverse class of substrates with a larger alcohol group than acid group have higher affinity for the CE2 enzyme (Imai, T. Human Carboxylesterase isozymes: Catalytic Properties and Rational Drug Design, (2006) Drug Metab. Pharmacokinet 21(3): 173-85).

The diacetate ester of the invention, 1-$^{13}$C-1,1-Bis(acetoxy(methyl))-2,2'-cyclopropane, is a substrate for the CE2 isoform.

It provides the advantage of being effectively hydrolyzed in liver, prostate and breast cells, where the CE2 enzyme is highly expressed. Especially in prostate cells, where the CE2 expression is high.

1-$^{13}$C-1,1-Bis(acetoxy(methyl))-2,2'-cyclopropane also provides good chemical and physical properties, as high solubility, high polarization, very long T1 (as compared to other compounds employed for metabolic imaging, illustrated in the following table 1), sufficient chemical shift separation between substrate and product to detect the hydrolysis product in vivo.

TABLE 1

T1 of 1-$^{13}$C-1,1-Bis(acetoxy(methyl-d$_2$))-2,2'-d$_4$-cyclopropane compared with other metabolic imaging compounds

| Compound | T1, 37 C. 14.1 T |
|---|---|
| 1-$^{13}$C-1,1-Bis(acetoxy(methyl-d$_2$))-2,2'-d$_4$-cyclopropane | 85 ± 4 |
| 1-13C-pyruvate | 45 ± 4 |
| 1-13C-acetate | 50 ± 3 |
| 1-13C-lactate | 40 ± 3 |
| 2-13C-1,1,2,2-d4-choline | 43 ± 4 |
| 1,3-ethyl acetoacetate | 27 ± 2 |
| 13C6-glucose | 15 ± 2 |
| 1-13C-glucose | 20 ± 2 |
| 1-13C-2-ketoisocaproate | 35 ± 4 |
| 1-13C-alanine | 31 ± 2 |
| 5-13C-glutamine | 22 ± 2 |
| 1,4-13C2-Fumarate | 35 ± 3 |
| 1,4-13C2-malate | 30 ± 3 |
| 1-13C-bicarbonate | 30 ± 2 |
| 1-13C-2-oxoglutarate | 30 ± 3 |

A further advantage of the use of the compound of the invention as a metabolic substrate is that its uptake into cells takes place mainly by diffusion through the cell membrane. Therefore, it is not uptake-limited and only the activity of the metabolizing enzyme itself has influence on the amount of hyperpolarized product that is produced. This means that the detected signal in the present invention is highly representative of the activity of the carboxylesterase, thus making said substrate particularly useful as real time molecular contrast agents. On the contrary, substrates like monocarboxylic acids, e.g. pyruvic acid, can suffer the disadvantage of being uptake-limited; the signal of their hyperpolarized product may therefore be not representative of the activity of the specific enzyme to be detected.

The method of the present invention is a non-invasive method, which allows a real time metabolic assessment of the carboxylesterase activity in vivo. An image representative of said activity is collected seconds to minutes following intravenous injection of the substrate.

Essentially, the method of operating an MRI system according to the present invention comprises the steps of a) recording an MR signal from the excited nuclei; and b) comparing a first MR signal deriving from the tumor or suspected tumor with a second MR signal deriving from the same subject or from a sample thereof.

In a preferred embodiment of the invention, said first signal deriving from said tumor is lower than said second MR signal.

In an embodiment of the present invention, as shown in steps d-f above, the MRI apparatus can process said first signal and said second signal by comparing each other, calculating a difference between the two signals and comparing said difference with a reference value; as shown in step g above, if this comparison provides a value which is, in absolute value, higher than a predetermined value, then said MRI apparatus provides an indication of possible tumor affection.

The use of said apparatus for monitoring the response of a subject affected by a tumor to antitumor therapy (step g') or for evaluating the aggressiveness of a tumor (step g") are further objects of the present invention.

Examples of said tumors are tumors selected from the group consisting of liver, colon, prostate and breast. In a preferred embodiment, the tumor is prostate tumor.

According to the present invention, the compound 1-$^{13}$C-1,1-Bis(acetoxy(methyl))-2,2'-cyclopropane can be exploited as a marker of targeted therapies, where for targeted therapy is intended the targeting of molecules important for the carcinogenesis of the cancer cells.

In carrying out the methods of the present invention, the first signal ($S_1$), the second signal ($S_2$) and the reference value (R), depend on how the methods of the invention are applied.

Typically, in order to have comparable data, the MR signals obtained in the method of the invention are normalized with respect to the corresponding signal of the 1-$^{13}$C-1,1-Bis(acetoxy(methyl)-2,2'-cyclopropane.

When the method of the present invention is performed to provide an indication of possible tumor affection, said first signal $S_1$, is the ratio between the integral of the MR line of the hyperpolarized metabolic product of the carboxylesterase conversion and the integral of the MR line of the administered substrate (the hyperpolarized 1-$^{13}$C-1,1-Bis(acetoxy(methyl)-2,2'-cyclopropane), detected in the region of interest comprising the alleged tumor, while the second signal $S_2$ is the analogue ratio calculated in non-tumor tissue; the reference value R is either equal to $S_2$ or, in case no signal of the hyperpolarized metabolic product is detected in the healthy tissue under consideration, R is set to 3 times the noise standard deviation divided by the substrate signal in the same volume. Preferably, non-tumor tissue is surrounding the tumor, so that the MR system can provide an accurate imaging of the tumor, which is of great importance for the evaluation of surgical intervention.

In case the purpose of the method is a follow-up of antitumor therapy, said first signal corresponds to the metabolic product signal detected in the tumor before, or at the start or at a certain point after the beginning of therapy and said second signal is the one produced by the same tumor after a certain period subsequent to the detection of said first signal. The reference value R is set equal to the first signal.

In case the purpose of the method is to determine aggressiveness of a tumor, said first signal is the one produced by the tumor at the start of the determination and said second signal is the one produced by the same tumor after a certain period subsequent to the detection of said first signal. Again the reference value is set equal to the first signal.

The first and second MR signals can be obtained either as single signals or calculated as a mean value of a plurality of respective signals determined (from different voxels) in a selected region of interest ($S_1$) or in a non-tumor tissue ($S_2$).

In an embodiment of the invention, said first signal and said second signal can be directly compared, either as single signals or as mean values of a plurality of signals, to obtain the desired information on the tumor tissue. In an alternative embodiment of the invention, the signals can be used to generate a parametric image and the comparison can be performed by comparing the zones of said image corresponding to said first and said second signal.

According to the present invention, a difference between said first and said second signal is determined. This difference ($S_1$-$S_2$) is important for the different scopes of the present invention.

This difference is compared with the reference value to produce a value representing the deviation (D) of said difference from said reference value:

$$D=(S_1-S_2)/R.$$

If it is determined that this deviation provides a value which is, in absolute value, higher than a predetermined value, this deviation provides an indication of possible tumor affection, of the efficacy of the antitumor therapy or of tumor aggressiveness, depending on the purpose of the method of the invention.

For instance, in an embodiment of the invention, said predetermined value can be set at 2; accordingly, if the calculated value "D" is equal or higher than 2, this can be indicative of a possible presence of a tumor in the region of interest, of the efficacy of the antitumor therapy or of tumor aggressiveness, depending on the purpose of the method of the invention. Preferably a deviation value D of from 2 to 10 can be indicative of said presence, efficacy or aggressiveness, more preferably a deviation from 2 to 20, even more preferably a deviation from 2 to 40, particularly preferred is a deviation from 2 to 60, maximally preferred is a deviation from 2 to 80, the most preferred is a deviation from 2 to 100 or higher.

In an embodiment of the invention, the method is performed on a subject who is suspected to suffer or suffers from a tumor.

In another embodiment of the present invention, the above method is performed on a subject who is undergoing or has been subjected to an antitumor treatment and the reference value is the signal of the hyperpolarized metabolic product(s) of the carboxylesterase conversion in said region of interest determined before, during or after said treatment. As above, if a deviation D is calculated which is higher, in absolute value, than a predetermined value (e.g. higher than 2, and preferably within the above indicated ranges), this provides an indication of the efficacy of the antitumor treatment.

In some embodiments, the present invention can be used in the field of so-called "personalized medicine", or similarly intended. As explained above, tumor therapy is affected by variations in its efficacy even on the same type of tumor and with the same anticancer therapeutic protocol. Such variations are due to the different individual responses by the patients. Carrying out the method of the present invention allows to monitor (follow-up) the efficacy of a tumor therapy and, in case, allowing the doctor to fit the therapy to the patient.

Typical metabolic imaging procedures with the compound of the invention in human subjects should be performed at magnetic fields ≥1 T. Field strengths of 1.5 T or higher are preferred since the spectral separation between the injected substrate (ester) and the observed metabolite (acid or alcohol) scales linearly with the intensity of the applied field. The MR scanner should be capable to detect $^{13}$C signals in addition to 1H and although not always mandatory, surface or endoscopic radiofrequency coils could allow achieving better results in specific organs. For prostate investigation for instance, an endorectal $^{13}$C is expected to strongly increase the sensitivity of the method with respect to a standard whole body resonator. Being the hyperpolarized signals typically available for a time range in the order of 3 to 5 times the longitudinal relaxation rate of 1-$^{13}$C-1,1-Bis(acetoxy(methyl))-2,2'-cyclopropane, the total acquisition time for a metabolic MR procedure will not exceed 5 min. Spectroscopic imaging sequences such as Single Voxel Spectroscopy (SVS) or Chemical Shift Imaging (CSI) need to be used in order to separate the signal coming from the substrate from that coming from the hyperpolarized metabolic product. Fast spectroscopic imaging sequences such as EPSI are preferred due to the limited time available for the acquisition.

In order for the method to provide enough sensitivity, 1-$^{13}$C-1,1-Bis(acetoxy(methyl))-2,2'-cyclopropane formulations and dissolution/transport protocols which allow to maintain at least 10% polarization at time of injection are preferred. Preferably, at least of about 20% polarization is maintained, more preferably at least of about 30% polarization is maintained, even more preferably at least of about 60% polarization is maintained, most preferably at least of about 80% polarization is maintained. Examples of said dissolution/transport protocols are described, for instance, in WO 02/36005.

The present invention will be further illustrated by the following examples.

EXAMPLES

Where not otherwise specified, chemicals and reagents used in the following examples are commercially available or can be prepared according to methods well-known in the art.

Example 1. Synthesis of 1-$^{13}$C-1,1-Bis(acetoxy (methyl-d$_2$))-2,2'-d$_4$-cyclopropane 284 mg, 2.55 mmol of 1-$^{13}$C-1,1-Bis(hydroxy(methyl-d$_2$))-2,2'-d$_4$-cyclopropane, (prepared as described by House, H. O. et al. "The synthesis of spiropentane-d8". J. Org. Chem. 1956, 21, 1487-149) were put in a glass flask and cooled to 0° C. on an ice bath. Acetyl chloride (3 ml, 34 mmol) was added slowly while stirring. After complete addition the mixture was allowed to warm to room temperature and stirred for additionally 12 h. The excess acetyl chloride and the formed hydrochloric gas were then removed in vacuum. The compound of formula (II) 1-$^{13}$C-1,1-Bis(acetoxy(methyl-d$_2$))-2,2'-d$_4$-cyclopropane was recovered as a colorless oil; yield: 445 mg (2.27 mmol, 90%).

Spectral data are consistent with the expected structure, as illustrated below:

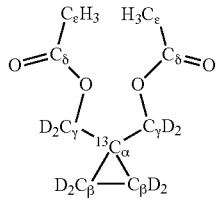

$^1$H NMR (Acetone-d$_6$, ppm): 2.01 (singlet)
$^{13}$C NMR (D$_2$O, ppm): 9.4 (multiplet, β), 19.6 (singlet, α, $^{13}$C label), 21.4 (singlet, ε), 70.1 (multiplet, γ), 175.8 (singlet, δ)

Example 2. Preparation of Hyperpolarized 1-$^{13}$C-1,1-Bis(acetoxy(methyl-d$_2$))-2,2'-d$_4$-cyclopropane A) Finland radical, carboxylic acid form (0.7 mg, 0.67 μmol) was dissolved in 1-$^{13}$C-1,1-Bis(acetoxy(methyl-d$_2$))-2,2'-d$_4$-cyclopropane (45 μl, 50.7 mg, 0.27 mmol). To the solution was added a DMSO solution of the gadolinium complex ([alfa1,alfa4,alfa7-tris[(phenylmethoxy)methyl]-1,4,7,10-tetraazacyclododecane-1,4,7,10-tetraacetato(4-)] gadolinate(1-)]hydrogen) (0.75 mg of a 100 μmol/g solution). The concentration of radical and gadolinium were 15 mM and 1.6 mM respectively.

B) 30 μmol of a 1-$^{13}$C-1,1-Bis(acetoxy(methyl-d$_2$))-2,2'-d$_4$-cyclopropane sample made following the description in example 2.A was hyperpolarized. The composition was hyperpolarised under DNP conditions at 1.2 K in a 3.35 T magnetic field under irradiation with microwave (93.900 GHz). The polarization build-up constant was 750 s. The solid-state polarization was approx. 15%.

C) The sample was dissolved in 5 ml phosphate buffer (40 mM, pH 7.3). The pH after dissolution was 7.3. The solution was collected directly into a 10 mm NMR tube and transferred to a 14.1 T magnet (pH 7.2) where a time series of 5 degree 1D $^{13}$C-NMR spectra were recorded with a total delay between the pulses of 3 s. The liquid state polarization was 13% (12 s after dissolution) and the liquid state T$_1$ was approx. 85 s at 14.1 T and 37 C. The 1-$^{13}$C-1,1-Bis(acetoxy (methyl-d$_2$))-2,2'-d$_4$-cyclopropane was not hydrolysed in the dissolution process, FIG. 1.

Example 3—Comparison Between Metabolism of Hyperpolarized 1-$^{13}$C-1,1-Bis(acetoxy(methyl-d$_2$))-2,2'-d$_4$-cyclopropane and Hyperpolarized 1-$^{13}$C-pyruvate in Rat Liver (Morris7777)

Materials and Methods

The experiments were performed with a co-polarization of 1-$^{13}$C-1,1-Bis(acetoxy(methyl-d$_2$))-2,2'-d$_4$-cyclopropane and 1-$^{13}$C-pyruvic acid in equal amounts of compounds (30 μmol) resulting in a concentration of approx. 3.5 mM of each substrate in the experiments. The DNP preparation of 1-$^{13}$C-1,1-Bis(acetoxy(methyl-d$_2$))-2,2'-d$_4$-cyclopropane was performed as described in example 2 and the DNP preparation of 1-$^{13}$C-pyruvate was performed as described in WO 2006/011809. The two substrates were co-polarized without mixing the substrates.

Rat liver cancer cells (Morris777) were grown in RPMI+ 10% FBS and antibiotics. Following trypsin harvesting 10 million cells were redissolved in 500 μl phosphate buffer (PBS) and transferred to a 10 mm NMR tube and placed with connecting tubing in a 14.1 T magnet at 37 C.

Following dissolution in 5 ml phosphate buffer (40 mM pH 7.3) with addition of 2.5 μl NaOH to neutralize the pyruvic acid 2 ml of the substrate mixture was injected into 10 million cells in suspension. A series of 20 degree pulses every 2 s (56 scans in total) was acquired. The acquisition was started just before injection of the hyperpolarized substrate. Data are presented as metabolite signals as a function of time or as area under the curve of the metabolite signals.

Results

An account of produced hyperpolarized 1-$^{13}$C-1-(acetoxy (methyl-d$_2$))-1-(hydroxy(methyl-d$_2$))-2,2'-d$_4$-cyclopropane and 1-$^{13}$C-lactate in rat liver cancer cells are shown in FIG. 2 and Table 2.

TABLE 2

Area under the metabolic curves for for two metabolites arising from 1-$^{13}$C-1,1-Bis(acetoxy(methyl-d$_2$))-2,2'-d$_4$-cyclopropane and from 1-$^{13}$C-lactate in Morris7777 cells.

| Metabolite | AUC (arb. Units) |
|---|---|
| 1-$^{13}$C-1-(acetoxy(methyl-d$_2$))-1-(hydroxy(methyl-d$_2$))-2,2'-d$_4$-cyclopropane | 43480 |
| 1-$^{13}$-1,1-(dihydroxy(methyl-d$_2$))-2,2'-d$_4$-cyclopropane | 1559 |
| 1-$^{13}$C-lactate | 282 |

It can be seen from this example that it is possible to follow the build-up of both the mono ester, 1-$^{13}$C-1-(acetoxy (methyl-d$_2$))-1-(hydroxy(methyl-d$_2$))-2,2'-d$_4$-cyclopropane and 1-$^{13}$C-1,1-(dihydroxy(methyl-d$_2$))-2,2'-d$_4$-cyclopropane resulting from the hydrolysis of hyperpolarized 1-$^{13}$C-1,1-Bis(acetoxy(methyl-d$_2$))-2,2'-d$_4$-cyclopropane in whole Morris7777 cells. It can also be appreciated that the metabolic conversion of hyperpolarized 1-$^{13}$C-1,1-Bis(acetoxy (methyl-d$_2$))-2,2'-d$_4$-cyclopropane is approx. 15 times higher than that of hyperpolarized 1-$^{13}$C pyruvate when comparing the maximum metabolite signal. Due to the very long T$_1$ of 1-$^{13}$C-1,1-Bis(acetoxy(methyl-d$_2$))-2,2'-d$_4$-cyclopropane the signal area under the curve of the mono-ester metabolite is significantly larger than the area under the curve of 1-$^{13}$C-lactate. This enables a potentially high quality image of the in vivo signal with the 1-$^{13}$C-1,1-Bis (acetoxy(methy-d$_2$))-2,2'-d$_4$-cyclopropane metabolite exploring an AUC which is almost 30 times that of 1-$^{13}$C-lactate.

Example 4. Carboxyl Esterase CE-2 Activities Measured with Hyperpolarized 1-$^{13}$C-1,1-Bis(acetoxy(methyl-d$_2$))-2,2'-d$_4$-cyclopropane in Human Prostate Cancer Cells (PC-3) in Comparison to Hyperpolarized 1-$^{13}$C-pyruvate Materials and Methods The experiments were performed with a co-polarization of 1-$^{13}$C-1,1-Bis(acetoxy(methyl-d$_2$))-2,2'-d$_4$-cyclopropane and 1-$^{13}$C-pyruvic acid in equal amounts of compounds (30 μmol) resulting in a concentration of approx. 3.5 mM of each substrate in the experiments. The DNP preparation of 1-$^{13}$C-1,1-Bis(acetoxy(methyl-d$_2$))-2,2'-d$_4$-cyclopropane was performed as described in example 2 and the DNP preparation of 1-$^{13}$C-pyruvate was performed as described in WO 2006/011809. The two substrates were co-polarized without mixing the substrates.

Human cancer cells (PC-3) were grown in RPMI+10% FBS and antibiotics. Following trypsin harvesting 10 million cells were redissolved in 500 μl phosphate buffer (PBS) and transferred to a 10 mm NMR tube and placed with connecting tubing in a 14.1 T magnet at 37° C.

Following dissolution in 5 ml phosphate buffer (40 mM pH 7.3) with addition of 2.5 μl NaOH to neutralize the pyruvic acid 2 ml of the substrate mixture was injected into 10 million cells in suspension. A series of 20 degree pulses every 2 s (56 scans in total) was acquired. The acquisition was started just before injection of the hyperpolarized substrate. Data are presented as metabolite signals as a function of time or as area under the curve of the metabolite signals.

Results

An account of produced hyperpolarized 1-$^{13}$C-1-(acetoxy (methyl-d$_2$))-1-(hydroxy(methyl-d$_2$))-2,2'-d$_4$-cyclopropane and 1-$^{13}$C-lactate in human prostate cancer cells are shown in FIG. 3 and Table 3.

TABLE 3

Area under the metabolic curves for 1-$^{13}$C-1-(acetoxy(methyl-d$_2$))-1-(hydroxy(methyl-d$_2$))-2,2'-d$_4$-cyclopropane and 1-$^{13}$C-lactate in PC-3 cells.

| Metabolite | AUC (arb. Units) |
|---|---|
| 1-$^{13}$C-1-(acetoxy(methyl-d$_2$))-1-(hydroxy(methyl-d$_2$))-2,2'-d$_4$-cyclopropane | 20550 |
| 1-$^{13}$C-lactate | 3766 |

It can be seen from this example that it is possible to follow the build-up of the mono ester, 1-$^{13}$C-1-(acetoxy (methyl-d$_2$))-1-(hydroxy(methyl-d$_2$))-2,2'-d$_4$-cyclopropane resulting from the hydrolysis of hyperpolarized 1-$^{13}$C-1,1-Bis(acetoxy(methy-d$_2$))-2,2'-d$_4$-cyclopropane in whole PC-3 cells. It can also be appreciated that the metabolic conversion of hyperpolarized 1-$^{13}$C-1,1-Bis(acetoxy (methyl-d$_2$))-2,2'-d$_4$-cyclopropane is more than 3 times higher than that of hyperpolarized 1-$^{13}$C pyruvate when comparing the maximum metabolite signal. Due to the very long T$_1$ of 1-$^{13}$C-1,1-Bis(acetoxy(methyl-d$_2$))-2,2'-d$_4$-cyclopropane the signal area under the curve of the mono-ester metabolite is significantly longer than the area under the curve of 1-$^{13}$C-lactate. This enables a potentially high quality image of the in vive signal with the 1-$^{13}$C-1,1-Bis (acetoxy(methyl-d$_2$))-2,2'-d$_4$-cyclopropane metabolite exploring an AUC which is almost 6 times that of 1-$^{13}$C-lactate.

Example 5. Carboxyl Esterase CE-2 Activities Measured with Hyperpolarized 1-$^{13}$C-1,1-Bis(acetoxy(methyl-d$_2$))-2,2'-d$_4$-cyclopropane in Human Prostate Cancer Cells (PC-3) in Comparison to Healthy Human Prostate Cells (PNT-1A)

Materials and Methods

The experiments were performed with a polarization of 1-$^{13}$C-1,1-Bis(acetoxy(methyl-d$_2$))-2,2'-d$_4$-cyclopropane (30 μmol) resulting in a concentration of approx. 3.5 mM of this substrate in the experiments. The DNP preparation of 1-$^{13}$C-1,1-Bis(acetoxy(methyl-d$_2$))-2,2'-d$_4$-cyclopropane was performed as described in example 2.

Human prostate cancer cells (PC-3) or immortalized human prostate healthy cells were grown in RPMI+10% FBS and antibiotics. Following trypsin harvesting 10 million cells were redissolved in 500 μl phosphate buffer (PBS) and transferred to a 10 mm NMR tube and placed with connecting tubing in a 14.1 T magnet at 37° C.

Following dissolution in 5 ml phosphate buffer (40 mM pH 7.3), 2 ml of the substrate mixture was injected into 10 million cells in suspension. A series of 20 degree pulses every 2 s (56 scans in total) was acquired. The acquisition was started just before injection of the hyperpolarized substrate. Data are presented as metabolite signals as a function of time or as area under the curve of the metabolite signals.

Results

An account of produced hyperpolarized 1-$^{13}$C-1,1-Bis (acetoxy(methyl-d$_2$))-2,2'-d$_4$-cyclopropane in prostate cancer and prostate healthy cells is shown in FIG. 4.

It can be seen from this example that it is possible to follow the build-up of the mono ester, 1-$^{13}$C-1-(acetoxy (methyl-d$_2$))-1-(hydroxy(methyl-d$_2$))-2,2'-d$_4$-cyclopropane resulting from the hydrolysis of hyperpolarized 1-$^{13}$C-1,1-Bis(acetoxy(methyl-d$_2$))-2,2'-d$_4$-cyclopropane in human prostate cancer PC-3 cells and in human healthy prostate cells. It can also be appreciated that the metabolic conversion of hyperpolarized 1-$^{13}$C-1,1-Bis(acetoxy(methyl-d$_2$))-2,2'-d$_4$-cyclopropane is approx. 6 times higher in the diseased cells than in the healthy cells. This difference suggests that a large contrast between diseased and healthy tissue can be expected in a human cancerous prostate.

Example 6: Conversion of Hyperpolarized 1-$^{13}$C-1,1-Bis(acetoxy(methyl-d$_2$))-2,2'-d$_4$-cyclopropane into Hyperpolarized 1-$^{13}$C-1-(acetoxy(methyl-d$_2$))-1-(hydroxy(methyl-d$_2$))-2,2'-d$_4$-cyclopropane and 1-$^{13}$C-1,1-Bis(hydroxy(methyl-d$_2$))-2,2'-d$_4$-cyclopropane in the Healthy Prostate of Living Rats Materials and Methods DNP-MRI experiment has been performed on 2 healthy Copenhagen rats, 9 weeks old, with average weight of 180 g.

0.24 mmol of a 1-$^{13}$C-1,1-Bis(acetoxy(methyl-d$_2$))-2,2'-d$_4$-cyclopropane sample prepared following the description in Example 2A was hyperpolarized according to the conditions reported in example 2.B. The solid sample was then dissolved in 5 ml TRIS buffer (100 mM, pH 7.7) to obtain a hyperpolarized solution with 48 mM substrate concentration and a pH of 7.

2.8 ml of the dissolved hyperpolarized 1-$^{13}$C-1,1-Bis(acetoxy(methyl-d$_2$))-2,2'-d$_4$-cyclopropane solution was injected intravenously at an injection rate of about 0.25 mL/s through a catheter placed in the tail vein of the animal, resulting in a total administered close of about 0.4 mmol/kg. A time series of 64 NMR spectra separated by 3 s and generated by 10° radiofrequency pulses was acquired starting from 15 s before injection of the hyperpolarized substrate. In order to follow the whole metabolic fate of the molecules and the decay of the hyperpolarized signal. The $^{13}$C MR signal was collected by a 20 mm surface coil placed around the prostate. Spatial localization of the signal has been achieved by combining the limited sensitivity volume of the receiving coil with a slice selective spectroscopic sequence including a single gradient kept on only during the excitation period.

Results

Hyperpolarized 1-$^{13}$C-1,1-Bis(acetoxy(methyl-d$_2$))-2,2'-d$_4$-cyclopropane is taken up by prostate cells and converted into its hyperpolarized metabolites, 1-$^{13}$C-1-(acetoxy(methyl-d$_2$))-1-(hydroxy(methy-d$_2$))-2,2'-d$_4$-cyclopropane and 1-$^{13}$C-1,1-Bis(hydroxy(methyl-d$_2$))-2,2'-d$_4$-cyclopropane, by a two steps metabolic process clearly observable, in vivo, on the time scale of the DNP experiment. A $^{13}$C NMR sum spectrum, obtained by integrating over time all the non-vanishing spectra of a time series acquired on a representative animal, is reported in FIG. 5. The chemical shift differences between the injected substrate and the relevant metabolic products are notable, allowing an unassailable identification of the different $^{13}$C labeled species which are present in the tissue under investigation. The time evolution of the hyperpolarized $^{13}$C signals of individual species is shown in FIG. 6. While the signal of 1-$^{13}$C-1,1-Bis(acetoxy(methyl-d$_2$))-2,2'-d$_4$-cyclopropane is decaying, the products signal firstly build up, due to metabolic conversion of 1-$^{13}$C-1,1-Bis(acetoxy(methyl-d$_2$))-2,2'-d$_4$-cyclopropane and then gradually decay according to their T$_1$ relaxation rate.

The invention claimed is:

1. A method for operating an MRI system comprising the steps of:
   a. administering a solution of hyperpolarized compound 1-$^{13}$C-1,1-Bis(acetoxy(methyl))-2,2'-cyclopropane to a subject who is affected or suspected to be affected by a tumor, submitting the subject to a radiation having a frequency selected to excite nuclear spin transitions in $^{13}$C nuclei;
   b. detecting an MR signal from said excited nuclei of at least one hyperpolarized metabolic product selected from the group consisting of 1-$^{13}$C-1-(acetoxy(methyl))-1-(hydroxy(methyl))-2,2'-cyclopropane and 1-$^{13}$C-1, 1-(dihydroxy(methyl))-2,2'-cyclopropane; and
   c. comparing a first MR signal deriving from a region of interest comprising said tumor or said suspected tumor with a second MR signal deriving from said subject or from a sample taken from said subject.

2. The method according to claim 1 further comprising the steps of:
   d. determining a difference between said first signal and second signal;
   e. comparing said difference of step d) with a reference value, to produce a deviation value; and
   f. determining if the deviation value is, in absolute value, higher than a predetermined value.

3. The method according to claim 2, wherein said second signal is determined on a non-tumor tissue, further comprising the step of:
   g. providing an indication of possible tumor affection in case the deviation value is in absolute value higher than said predetermined value.

4. The method according to claim 2, wherein said second signal is determined in the region of interest, at an earlier moment in time with respect to the first signal, and optionally stored in the system, said method further comprising the step of:
   g' providing an indication of tumor variation in case the deviation is in absolute value higher than said predetermined value.

5. The method according to claim 2, wherein said subject has undergone an anti-tumor treatment and wherein said second signal is determined in the region of interest, at an earlier moment in time with respect to said first signal, and optionally stored in the system, said method further comprising the step of:
   g" providing an indication of efficacy of said treatment if this deviation is in absolute value higher than a predetermined value.

6. The method according to claim 5 wherein said second signal is determined before, after or at the beginning of the treatment.

7. A method for operating an MRI system comprising the steps of:
   a. administering a solution of hyperpolarized deuterated compound 1-$^{13}$C-1,1-Bis(acetoxy(methyl))-2,2'-cyclopropane of formula (II):

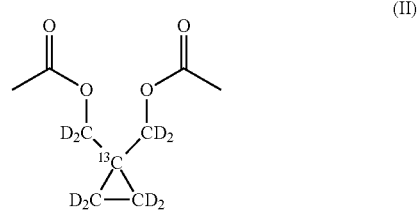

(II)

to a subject who is affected or suspected to be affected by a tumor, submitting the subject to a radiation having a frequency selected to excite nuclear spin transitions in $^{13}$C nuclei;
   b. detecting an MR signal from said excited nuclei of at least one hyperpolarized metabolic product selected from the group consisting of 1-$^{13}$C-1-(acetoxy(methyl-d$_2$))-1-(hydroxy(methyl-d$_2$))-2,2'-d$_4$-cyclopropane and 1-$^{13}$C-1, 1-(dihydroxy(methyl-d$_2$))-2,2'-d$_4$-cyclopropane; and
   c. comparing a first MR signal deriving from a region of interest comprising said tumor or said suspected tumor with a second MR signal deriving from said subject or from a sample taken from said subject.

8. The method according to claim 7 further comprising the steps of:
   d. determining a difference between said first signal and second signal;

e. comparing said difference of step d) with a reference value, to produce a deviation value; and
f. determining if the deviation value is, in absolute value, higher than a predetermined value.

9. The method according to claim 8, wherein said second signal is determined on a non-tumor tissue, further comprising the step of:
g. providing an indication of possible tumor affection in case the deviation value is in absolute value higher than said predetermined value.

10. The method according to claim 8, wherein said second signal is determined in the region of interest, at an earlier moment in time with respect to the first signal, and optionally stored in the system, said method further comprising the step of:
g' providing an indication of tumor variation in case the deviation is in absolute value higher than said predetermined value.

11. The method according to claim 8, wherein said subject has undergone an anti-tumor treatment and wherein said second signal is determined in the region of interest, at an earlier moment in time with respect to said first signal, and optionally stored in the system, said method further comprising the step of:
g" providing an indication of efficacy of said treatment if this deviation is in absolute value higher than a predetermined value.

12. The method according to claim 11 wherein said second signal is determined before, after or at the beginning of the treatment.

* * * * *